United States Patent
Allegretti et al.

(10) Patent No.: US 6,835,734 B2
(45) Date of Patent: Dec. 28, 2004

(54) 1,3-DIOXOLANES WITH ANTITUSSIVE ACTIVITY

(75) Inventors: Marcello Allegretti, L'Aquila (IT); Maria Candida Cesta, L'Aquila (IT); Roberto Curti, L'Aquila (IT); Luigi Pellegrini, L'Aquila (IT); Gabriella Melillo, L'Aquila (IT)

(73) Assignee: Dompé S.p.A., L'aquila (IT)

( * ) Notice: Subject to any disclaimer, the term of this patent is extended or adjusted under 35 U.S.C. 154(b) by 0 days.

(21) Appl. No.: 10/333,979

(22) PCT Filed: Jul. 18, 2001

(86) PCT No.: PCT/EP01/08304

§ 371 (c)(1),
(2), (4) Date: May 12, 2003

(87) PCT Pub. No.: WO02/10149

PCT Pub. Date: Feb. 7, 2002

(65) Prior Publication Data

US 2004/0038989 A1 Feb. 26, 2004

(30) Foreign Application Priority Data

Jul. 28, 2000 (IT) .................. MI2000A1734

(51) Int. Cl.$^7$ .................. A61K 31/496; C07D 405/06
(52) U.S. Cl. .................. 514/254.1; 544/230; 544/374
(58) Field of Search .................. 544/230, 374; 514/254.1

(56) References Cited

U.S. PATENT DOCUMENTS

2003/0176446 A1 * 9/2003 Allegretti et al. ........ 514/254.1

FOREIGN PATENT DOCUMENTS

| EP | 0 147 847 A | 7/1985 |
|---|---|---|
| EP | 0 349 066 A | 1/1990 |
| EP | 0 575 776 A | 12/1993 |
| FR | 2 634 765 A | 2/1990 |
| WO | WO 93 16056 A | 8/1993 |

* cited by examiner

*Primary Examiner*—Emily Bernhardt
(74) *Attorney, Agent, or Firm*—Birch, Stewart, Kolasch & Birch, LLP

(57) ABSTRACT

(S)-3-(4-Phenyl-1-piperazinyl)-1,2-propanediol cyclic acetals useful as antitussive agents and as intermediates for the preparation of levodropropizine and the salts thereof, as well as a process for the preparation of said acetals, are disclosed.

8 Claims, No Drawings

1,3-DIOXOLANES WITH ANTITUSSIVE ACTIVITY

This application is the national phase under 35 U.S.C. § 371 of PCT International Application No. PCT/EP01/08304 which has an International filing date of Jul. 18, 2001, which designated the United States of America.

The present invention relates to (S)-3-(4-phenyl-1-piperazinyl)-1,2-propanediol cyclic acetals useful as antitussive agents and as intermediates for the preparation of levodropropizine and the salts thereof. The invention also relates to a process for the preparation of said acetals.

More precisely, the present invention relates to (S)-2,2-substituted-1,3dioxolanes of formula (1):

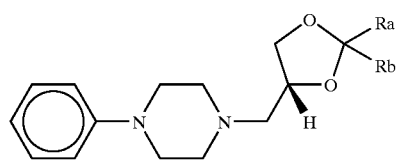

wherein:
each of Ra and Rb, which can be the same or different, is hydrogen, $C_1$–$C_6$-alkyl, phenyl; or Ra and Rb, taken together with the C atom they are linked to, form an optionally substituted 4- to 7-membered carbocyclic ring.

Preferred compounds of formula (1) are those wherein Ra and Rb are alkyl groups containing less than 6 C atoms. Preferably, Ra and Rb are the same; more preferably, Ra and Rb are methyl or ethyl or, together with the C atom they are linked to, form a ring containing 5 to 6 carbon atoms.

The invention also relates to the enantiomerically pure monobasic salts of the (S)-2,2-substituted-1,3-dioxolanes of formula (1) with pharmaceutically acceptable acids. Particularly preferred pharmaceutically acceptable acids are acetic, propionic, succinic, fumaric, maleic, L-malic, D- and L-tartaric, D- and L-mandelic, L and D-camphorsulfonic acids.

Particularly preferred compounds of the invention are:
S(−)-1,2-cyclopentylidene-3-(4-phenyl-piperazin-1-yl)-propane-1,2-diol;
S(−)-1,2-cyclohexylidene-3-(4-phenyl-piperazin-1-yl)-propane-1,2-diol;
S(−)-1,2-(2-propylidene)-3-(4-phenyl-piperazin-1-yl)-propane-1,2-diol;
S(−)-1,2-(3-pentylidene)-3-(4-phenyl-piperazin-1-yl)-propane-1,2-diol;
S(−)-1,2-cyclohexylidene-3-(4-phenyl-piperazin-1-yl)-propane-1,2-diol maleate;
S(−)-1,2-cyclohexylidene-3-(4-phenyl-piperazin-1-yl)-propane-1,2-diol L-tartrate;
S(−)-1,2-cyclohexylidene-3-(4-phenyl-piperazin-1-yl)-propane-1,2-diol fumarate;
S(−)-1,2-cyclohexylidene-3-(4-phenyl-piperazin-1-yl)-propane-1,2-diol D-10-camphorsulfonate.

The compounds of the invention of formula (1) are obtained by reacting phenylpiperazine with a (R)-1,2-glyceryl-dioxolane of formula (2):

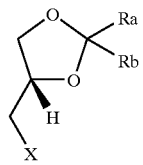

wherein X is selected from the group consisting of Cl, Br, I and a suitable sulfonic ester (R—SO$_3$—), wherein R is $C_1$–$C_3$-alkyl, trifluoromethyl, phenyl, p-tolyl or p-methoxyphenyl.

The dioxolanes of formula (2) are known compounds and/or can be prepared by using known methods.

More particularly, the sulfonic esters of formula (2) (X=R—SO$_3$—) are prepared with conventional methods using use of an anhydride or a chloride of an alkyl- and/or aryl-sulfonic acid of formula (3):

R—SO$_3$H (3)

to esterify an (R)-2,2-substituted-1,3-dioxolane-4-methanol of formula (4):

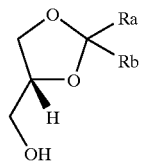

wherein Ra and Rb have the meanings defined above.

The 1,3-dioxolane-4-methanols of formula (4) are also known compounds, and the preparation thereof is widely described in literature. For example, they can be obtained by fermentative resolution of the racemates of formula (4) according to the process disclosed in U.S. Pat. No. 5,190,867 (Feb. 3, 1993) or, preferably, by oxidative degradation of D-mannitol 1,2;5,6-bis-dioxolanes, following substantially the process described by Borsa et al. in EP 147.847 (7 Mar. 1990), used for the preparation of (+)-1,2-isopropylidene-sn-glycerol (formula (4) wherein Ra and Rb are methyl) and of the tosylate thereof (formula (3) wherein Ra and Rb are methyl and R is p-tolyl).

Useful teachings for the preparation of the D-mannitol 1,2;5,6-bis-dioxolanes and of the corresponding D-glyceraldehyde acetals can also be found in J. Org. Chem. 56, 4056 (1991) and in Synthesis 587 (1992), where the preparation of 2,3-O-(3-pentylidene)-D-glyceraldehyde in 55% yields from D-mannitol is specifically described.

4-Halomethyl-dioxolanes of formula (2) wherein X is Cl, Br or I can in turn be prepared starting from the corresponding sulfonic esters of formula (2) (X=RSO$_3$— wherein R is as defined above) by reaction with a suitable alkali or alkaline-earth (Na, K or Ca) halide in an inert solvent selected from the group consisting of acetone, methyl ethyl ketone, tetrahydrofuran, dioxane, dimethylsulfoxide, acetonitrile, a $C_1$–$C_4$-alcohol and mixtures thereof.

Alternatively, dioxolanes of formula (2) (X=Cl, Br) can be prepared by dioxolanation of the corresponding 3-halo-1,2-propanediols, as disclosed in EP 0.930.311 (21 Jul. 1999). Particularly preferred is 3-chloro-propanediol. Preferred acetalyzing agents are formaldehyde, acetaldehyde and benzaldehyde, acetone, diethyl ketone, benzophenone, cyclohexanone, the acetals or enolethers thereof such as 2,2-dimethoxypropane, 2,2-dimethoxyethane and 2-methoxy-propene.

Alternatively, dioxolanes of formula (2) (X=Cl, Br) can also be prepared by acetalyzation of chiral epichlorohydrins or epibromohydrins or of the corresponding chiral 3-halo-propanediols with a cycloalkanone according to the processes described for the preparation of (±)2-chloromethyl-1,4-dioxaspiro[4,5]-decane in FR 1.522.153 or more generally by Blicke F F et al., J. A. C. S, 74, 1735 (1972) and ibidem, 76, 1226 (1954).

Said chiral epichlorohydrins or epibromohydrins and the corresponding 3-halo-propanediols are in their turn easily available intermediates, obtainable for example by kinetic resolution of the respective racemates [according to Furrow et al., J.Org. Chem., 63, 6776, 1998 or alternatively according to T. Takeichi et al., Tetrahedron, 36, 3391 (1980)] or by enzymatic resolution (see Kasai N et al., JP 02257895 (1990); C.A: 114, 41064q, 1991).

Phenylpiperazine is alkylated with a 1,2-glyceryl-dioxolane of formula (2) using conventional reaction conditions for the conversion of a secondary amine into a tertiary amine, using for each mol of alkylating agent of formula (2) at least one mol or a slight molar excess of phenylpiperazine in the presence of at least one mol of a counterbase.

The counterbase is selected from the group consisting of finely divided inorganic bases such as alkali or alkaline-earth (Na, K, Mg, Ca) carbonates or bicarbonates or Ca or Mg oxides, or tertiary amines as triethylamine, dimethyl or diethylaniline, aromatic amines as pyridine, picoline and collidine and, if desired, the phenylpiperazine itself which may be subsequently recycled to a subsequent production cycle.

The alkylation reaction can be performed in the hot, optionally in the presence of inert solvents such as toluene and/or xylene which, when operating under reflux of the solvent, will advantageously reduce the reaction times.

After completion of the alkylation reaction, any insolubles are filtered or centrifuged off, then the organic phases are repeatedly washed with water to easily remove the impurities and side-products, and the solvent is distilled off to obtain in high yields a residue consisting of a substantially pure 1,3-dioxolane of the invention of formula (1), which is recovered either by direct crystallization or after salification with the desired pharmaceutically acceptable acid.

Compounds (1) and the salts thereof are suprisingly easy to crystallize from the usual solvents: the process of the invention therefore minimizes any risks of contaminations due to the presence of glycidols and/or epihalohydrins traces as potential impurities.

The monobasic salts of the compounds of formula (1) are obtained by using conventional methods such as salification with equimolecular amounts of the desired acid in a suitable solvent and subsequent crystallization of the resulting salt.

Furthermore, the compounds of the invention of formula (1) and the monobasic salts thereof are substantially tasteless and do not have the bitter after-taste typical of levodropropizine. Compounds (1) are efficient pro-drugs of levodropropizine, in that aqueous solutions of 1,3-dioxolanes of formula (1) and of the salts thereof are converted to levodropropizine by hot hydrolysis catalyzed by a molar excess of a diluted mineral acid such as hydrochloric acid, or of a water-miscible carboxylic acid such as acetic, malonic or citric acids.

The compounds of formula (1) and the aqueous solutions of the monobasic salts thereof are quite stable at physiological pH.

The compounds of the invention and the salts thereof have per se antitussive activity, as evidenced by the results of comparative tests through the intravenous route carried out in comparison with levodropropizine itself. Said activity is not due to conversion to levodropropizine.

The tests were carried out on male Dunkin-Hartley Guinea pigs (4–6 animals for group), which were subjected to aerosol of a 0.0045% (p/v) capsaicin aqueous solution [Lavezzo A., *Pulm. Pharmacol.*, 5, 143–147, 1992; Gallico L. et al, *Br. J. Pharmacol.*, 112, 795–800. 1994] 5 minutes after intravenous administration of 0.5 ml of a (-)-1,2-cyclohexylidene-3-(4-phenyl-piperazin-1-yl)-propane-1,2-diol fumarate solution (DF 1689A, 10 mg/kg) compared with 0.5 ml of a levodropropizine solution, pH 4.5 (10 mg/kg) and with an equal volume of saline solution (control). Cough strokes were recorded during the 4 minute capsaicin aerosol, thereby evidencing a significant inhibition (47.3%) of the response to the tussigenic stimulus compared with a 43.6% inhibition calculated for the control.

In fact, the recorded cough strokes were the following:
9.17±1.01 for the control animals,
5.17±0.54 for levodropropizine-treated animals,
4.83±0.54 for the animals treated with the compound of the invention DF 1689A.

The antitussive action is further characterized by a long lasting effect: inhibition values of 34.6 and 27.3% on the tussigen stimulus induced by aerosol administration of the capsaicin solution were in fact calculated 15 and 30 minutes after the intravenous administration.

The compounds of formula (1) and the salts thereof can suitably be administered also through aerosol; in fact, male Dunkin-Hartley Guinea pigs subjected to aerosol with 1% (w/v) aqueous solutions of DF 1689A and of levodropropizine for 10 minutes, showed a remarkable reduction of the number of cough strokes induced by the two medicaments compared with controls (saline solution aerosol) with an about 35% inhibitory effect for both medicaments.

For use as antitussive agents, compounds (1) will be formulated in pharmaceutical compositions according to conventional techniques and excipients, for the administration through the oral, parenteral or aerosol routes, for example in the form of capsules, gastro-resistant tablets, syrups, controlled-release formulations.

The mean daily dosage will depend on various factors, such as the frequency and, severity of the cough strokes and the general conditions of the patient (age, sex and weight). The daily dosage for an adult subject weighing 60 kg will vary from about ten mg to 1500 mg of the compounds of formula (1) daily, optionally distributed in multiple administrations. The compounds of the invention may also be administered to children, even for long times, suitably adjusting the dosages, thanks to their low toxicity.

Finally, the compounds of the invention are useful intermediates for the preparation of levodropropizine and the salts thereof.

The following examples further illustrate the invention.

EXAMPLE 1

To a solution of 13.8 g of humid 1,2:5,6-Di-O-(3-pentylidene)-D-mannitol, prepared according to the process described in Synthesis, 587, 1992) in tetrahydrofuran (THF) cooled to 20–25° C., a suspension of potassium periodate (7.95 g) and potassium bicarbonate (0.32 g) in water (50 ml) is added in 10 min. The mixture is stirred vigorously for three hours, cooled to 5° C. and filtered. The precipitated potassium iodate is washed with ethyl acetate and the two combined phases are left to warm to room temperature. The aqueous phase is treated with NaCl and repeatedly extracted with ethyl acetate. The combined organic phases are added, under strong stirring, with a solution of 3.2 g of $NaBH_4$ and 1.88 g of tetrabutylammonium bromide in 120 ml of water. The mixture is reacted for 3 h at r.t., the phases are separated, the aqueous phase is extracted with ethyl acetate (2×30 ml), filtered, dried over sodium sulfate, and the solvent is evaporated off under vacuum. The resulting oily residue is distilled under reduced pressure to obtain 7.12 g of 2,3-O-(3-pentylidene)-D-glycerol, $[\alpha]_D$=+17.2 (EtOH).

To a solution of 6.45 g of this alcohol in ethyl acetate (18 ml) are added, in succession, 6 ml of triethylamine then, under stirring and with external cooling, a solution of 7.76 g of p-toluenesulfonyl chloride in AcOEt (18 ml). The mixture is stirred for 12 h at r.t., then diluted with water (10 ml) and the phases are separated and repeatedly washed with water (3×10 ml), dried over sodium sulfate, filtered and evaporated to dryness under reduced pressure to obtain 11.98 g of 2,3-O-(3-pentylidene)-D-glycerol tosylate, $[\alpha]_D$=−4 (DMF).

To a solution of the tosylate in n-butanol (70 ml) are added in the order and under strong stirring 4.5 g of finely divided sodium carbonate and 6 ml of phenylpiperazine. The mixture is refluxed under stirring, then reacted at the reflux temperature for 20 h. Butanol is then evaporated off under reduced pressure, the residue is taken up with water and repeatedly extracted with ethyl acetate. The combined organic phases are dried and filtered, then the solvent is evaporated off under vacuum. The resulting residue is crystallized from aqueous methanol to obtain 8.95 g of S(−) 1,2-(3-pentylidene)-3-(4-phenyl-piperazin-1-yl)-propane-1, 2-diol, also named 4-phenylpiperazine, 1-(2,2-diethyl-1,3-dioxolan-4-yl-methyl).

EXAMPLE 2

Following the procedure described in Example 1, using 2,3-O-(2-propylidene)-D-glycerol tosylate, S(−) 1,2-(2-propylidene)-3-(4-phenyl-piperazin-1-yl)-propane-1,2-diol, also named 4-phenylpiperazine, 1-(2,2-dimethyl-1,3-dioxolan-4-yl-methyl), is obtained.

EXAMPLE 3

A solution of 3.1 g of 2,3-O-(3-cyclohexylidene)-D-glycerol, $[\alpha]_D$=+15.6 (EtOH) in dichloromethane (10 ml) is added, under inert gas atmosphere, with 2.8 ml of triethylamine and then, after cooling to about 15° C., with a solution of 1.44 ml of methanesulfonyl chloride in 2 ml of dichloromethane, drop by drop, preventing the reaction mixture inner temperature from exceeding 30° C. The resulting suspension is stirred for 1 h at room temperature, then diluted with ice-water. The organic phase is separated, washed with water, decolorized with active carbon and evaporated under vacuum to give a residue of 4.3 g of 2,3-O-(3-cyclohexylidene)-D-glycerol mesylate, $[\alpha]_D$=−3,3 ($CHCl_3$).

$^1$H NMR δ 4.37 (m,1H); δ 4.24 (m, 2H); δ 4.1 (dd, 1H, $J_1$=8.7 Hz, $J_2$=6.4 Hz); δ 3.8 (dd, 1H, $J_1$=8.7 Hz, $J_2$=5.4 Hz); δ 3.1 (s, 3H); δ 1.7,1.3 (m, 10H).

A solution of the mesylate in toluene (16 ml) is added with 5.45 ml of penylpiperazine, the mixture is then refluxed until completion of the reaction (approximately 8 hours). The reaction mixture is cooled to about 50° C., added with 10 ml of water and kept under strong stirring for at least 10 minutes. The phases are separated, then the organic phase is repeatedly washed with water. The solvent is evaporated off to obtain a thick oil which is dissolved while hot in isopropanol (15 ml). The solution is then slowly cooled, to separate a crystalline solid of S(−)-1,2-cyclohexylidene-3-(4-phenyl-piperazin-1-yl)propane-1,2-diol.

63–64° C., $[\alpha]_D$=−7.8° (1% MeOH). $^1$H NMR δ 7.26 (t, 2H, J=7.4 Hz); δ 6.95 (d, 2H, J=8.9 Hz); δ 6.85 (t, 1H, J=7.28 Hz); δ 4.3 (m, 1H, J=6.1 Hz); δ 4.1 (dd, 1H, $J_1$=8.0 Hz, $J_2$=6.1 Hz); δ 3.65 (dd, 1H, $J_1$=8.0. J2=7.1 Hz); δ 3.2 (t, 4H, J=5.05 Hz); δ 2.9, 2.55 (m, 6H); δ 1.7, 1.3 (m, 10H)

EXAMPLE 4

Following the procedure described in Examples 1 and 3, by reacting a 1,3-dioxolane selected from the group consisting of:

2S-1,4-dioxaspiro[4.4]nonane-2-methanol, p-toluenesulfonate;

2S-1,4-dioxaspiro[4.4]nonane-2-chloromethyl;

2S-1.4-dioxaspiro[4.5]decane-2-methanol trifluoromethanesulfonate;

2S-1,4-dioxaspiro-[4.5]decane-2-chloromethyl;

2S-1,3-dioxolane-4-chloromethyl-2,2-dimethyl;

2S-1,3-dioxolane-4-iodo-methyl-2,2-dimethyl;

with phenylpiperazine, the following compounds were obtained:

S(−)-1,2-cyclopentylidene)-3-(4-phenyl-piperazin-1-yl)-propane-1,2-diol;

S(−)-1,2-cyclohexylidene-3-(4-phenyl-piperazin-1-yl) propane-1,2-diol;

S(−)-1,2-(2-propylidene)-3-(4-phenyl-piperazin-1-yl)-propane-1,2-diol.

EXAMPLE 5

0.232 g of fumaric acid are added under stirring to a solution of S(−)-1,2-cyclohexylidene-3-(4-phenyl-piperazin-1-yl)propane-1,2-diol (0.632 g) in absolute ethanol (8 ml). The mixture is stirred until complete dissolution, then solvent is evaporated off under vacuum and the solid residue is crystallized from acetone, to obtain a crystalline solid of S(−)-1,2-cyclohexylidene-3-(4-phenyl-piperazin-1-yl)propane-1,2-diol fumarate (DF1689A, 0.52 g), m.p. 162–164° C., $[\alpha]_D$=−15.7 (c=1%; $CH_3OH$).

$^1$H NMR δ 7.5 (dd, 2H, $J_1$=8.7 $J_2$=7.3); δ 7.2 (m, 3H); δ 6.75 (s, 2H); δ 4.8 (m, 1H); δ 4.35 (dd, 1H, $J_1$=8.9 Hz $J_2$=6.7 Hz); δ 3.86 (dd, 1H, $J_1$=8.9 Hz $J_2$=5.8 Hz); δ 3.6–3.4 (m, 10H); δ 1.8–1.48 (m, 10H)

EXAMPLE 6

By salification of S(−)-1,2-cyclohexylidene-3-(4-phenyl-piperazin-1-yl)propane-1,2-diol with L-tartaric, maleic, D(+)-10-camphorsulfonic, L-mandelic acids, the following compounds were obtained:

S(−)-1,2-cyclohexylidene-3-(4-phenyl-piperazin-1-yl) propane-1,2-diol, L-tartrate, m.p. 130–132° C., $[\alpha]_D$=−9.7° (c=1%; MeOH);

S(−)-1,2-cyclohexylidene-3-(4-phenyl-piperazin-1-yl) propane-1,2-diol, maleate, m.p. 160–162° C., $[\alpha]_D$=−23.6 (c=1%; $CH_3OH$);

S(−)-1,2-cyclohexylidene-3-(4-phenyl-piperazin-1-yl) propane-1,2-diol, D(+)-10-camphorsulfonate, m.p. 110–115° C.,$[\alpha]_D$=−3.9 (c=1%; $CH_3OH$);

S(−)-1,2-cyclohexylidene-3-(4-phenyl-piperazin-1-yl) propane-1,2-diol, L-mandelate $[\alpha]_D$=+26.8 (c=1%; $CH_3OH$).

EXAMPLE 7

A suspension of 3.5 g of S(−)-1,2-cyclohexylidene-3-(4-phenyl-piperazin-1-yl)-propane-1,2-diol in 70 ml of aqueous acetic acid (10% w/v) is refluxed for 2h, then vapor is bubbled therein to distil cyclohexanone, which is separated. The aqueous phase is neutralized to pH 7 by addition of a 10% NaOH solution, then cooled to 5–10° C., to obtain 2.05 g of (−) 3-(4-phenyl-piperazin-1-yl)-propanediol, m.p. 102–103° C., $[\alpha]_D=-23.5°$ (2,8% $CH_2Cl_2$).

EXAMPLE 8

Alternatively, 0.35 molar equivalents of one of the 1,3-dioxolane derivatives described in Examples 1–4, namely S(−)-1,2-(2-propylidene)-3-(4-phenyl-piperazin-1-yl)-propane-1,2-diol; S(−)-1,2-cyclopentylidene)-3-(4-phenyl-piperazin-1-yl)-propane-1,2-diol; S(−)-1,2-cyclohexylidene-3-(4phenyl-piperazin-1-yl)propane-1,2-diol; S(−)-1,2-(2-propylidene)-3-(4-phenyl-piperazin-1-yl)-propane-1,2-diol, are added in portions to a 36% hydrochloric acid solution (36 ml) in 45 ml of water under stirring; the suspension is heated to 80° C. to obtain a clear solution which is kept at this temperature for a further 30 minutes, then cooled to 20–25° C. The aqueous phase is repeatedly extracted with dichloromethane (3×15 ml), then n-butanol (0.5 L) is added. The diphasic mixture is refluxed to distil the water-n-butanol azeotropic mixture, recovering about 300 ml of distillate, then cooled to promote crystallization of (−) 3-(4-phenyl-piperazin-1-yl)-propanediol hydrochloride (85 g).

A solution of the hydrochloride in 125 ml of water is decolorized with active charcoal (2.2 g) by heating to 50° C. for 15 minutes, filtered and subsequently neutralized by addition of an ammonium hydroxide aqueous solution (30% w/w). After briefly heating to 50° C., crystallization is started by addition of (−) 3-(4-phenyl-piperazin-1-yl)-propanediol crystals. The suspension is left to spontaneously cool, then kept for 2 hours at +2+4° C., and filtered to yield 70–72 g of (−) 3-(4-phenyl-piperazin-1-yl)-1,2-propanediol.

What is claimed is:

1. A compound of formula (1):

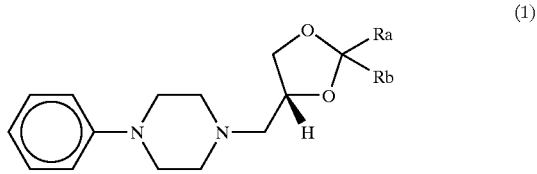

(1)

wherein:
each of Ra and Rb, which can be the same or different, is hydrogen, $C_1$–$C_6$-alkyl, phenyl; or Ra and Rb, taken together with the C atom they are linked to, form a 4- to 7-membered carbocyclic ring, or a salt thereof.

2. The compound as claimed in claim 1, wherein Ra and Rb are the same.

3. The compound as claimed in claim 1, wherein each of Ra and Rb is methyl or ethyl.

4. A compound selected from the group consisting of:
S(−)-1,2-cyclopentylidene-3-(4-phenyl-piperazin1-yl)-propane-1,2-diol;

S(−)-1,2-cyclohexylidene-3-(4-phenyl-piperazin-1-yl)-propane-1,2-diol;

S(−)-1,2-(2-propylidene)-3-(4-phenyl-piperazin-1-yl)-propane-1,2-diol;

S(−)-1,2-(3-pentylidene)-3-(4-phenyl-piperazin-1-yl)-propane-1,2-diol;

S(−)-1,2-cyclohexylidene-3-(4-phenyl-piperazin-1-yl)-propane-1,2-diol maleate;

S(−)-1,2-cyclohexylidene-3-(4-phenyl-piperazin-1-yl)-propane-1,2-diol fumarate; and S(−)-1,2-cyclohexylidene-3-(4-phenyl-piperazin-1-yl)-propane-1,2-diol D-10-camphorsulfonate.

5. A process for the preparation of a compound of formula (1):

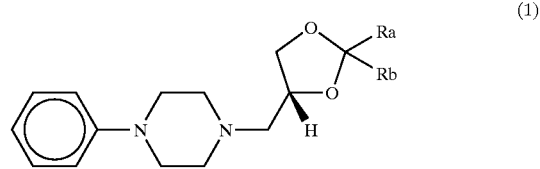

(1)

wherein each of Ra and Rb, which can be the same or different, is hydrogen, $C_1$–$C_6$-alkyl, phenyl; or Ra and Rb, taken together with the C atom they are linked to, form a 4- to 7-membered carbocyclic ring, and salts thereof, comprising the steps of:

reacting phenylpiperazine with a (R)1,2-glyceryl-dioxolane of formula (2):

(2)

wherein X is selected from the group consisting of Cl, Br, I and a suitable sulfonic ester (R—SO₃—), wherein R is $C_1$–$C_3$-alkyl, trifluoromethyl, phenyl, p-tolyl or p-methoxyphenyl; and recovering the compound of formula (1).

6. The process as claimed in claim 5, wherein the reaction is carried out in the presence of a base and using toluene or xylene as solvents.

7. A pharmaceutical composition comprising the compound as claimed in any one of claims 1–4 in mixture with suitable carriers.

8. A method for treating coughing, comprising the step of administering the compound as claimed in any one of claims 1–4 to a subject in need thereof.

* * * * *